(12) United States Patent
Xing et al.

(10) Patent No.: US 10,386,274 B2
(45) Date of Patent: Aug. 20, 2019

(54) PLUG-IN AIR QUALITY DETECTOR, CONTROL METHOD AND CONTROL DEVICE

(71) Applicant: Beijing Xiaomi Mobile Software Co., Ltd., Beijing (CN)

(72) Inventors: Zheng Xing, Beijing (CN); Ningning Li, Beijing (CN); Lei Zhang, Beijing (CN)

(73) Assignee: Beijing Xiaomi Mobile Software Co., Ltd., Beijing (CN)

( * ) Notice: Subject to any disclaimer, the term of this patent is extended or adjusted under 35 U.S.C. 154(b) by 147 days.

(21) Appl. No.: 15/467,769

(22) Filed: Mar. 23, 2017

(65) Prior Publication Data
US 2017/0284906 A1 Oct. 5, 2017

(30) Foreign Application Priority Data
Mar. 29, 2016 (CN) .......................... 2016 1 0189032

(51) Int. Cl.
*G01N 1/22* (2006.01)
*F24F 11/30* (2018.01)
(Continued)

(52) U.S. Cl.
CPC ............ *G01N 1/2273* (2013.01); *F24F 11/30* (2018.01); *G01N 15/06* (2013.01);
(Continued)

(58) Field of Classification Search
CPC .. G01N 1/2273; G01N 15/06; G01N 33/0027; G01N 33/0062; G01N 33/0073; F24F 11/30; H04M 1/21
(Continued)

(56) References Cited

U.S. PATENT DOCUMENTS 7,755,481 B2 * 7/2010 Gayden .................. G08B 7/06
340/539.26
2008/0045156 A1 2/2008 Sakhpara
(Continued)

FOREIGN PATENT DOCUMENTS

CN 201508339 U 6/2010
CN 202141709 U 2/2012
(Continued)

OTHER PUBLICATIONS

International Search Report issued in corresponding PCT Application No. PCT/CN2016/098262, dated Dec. 27, 2016, 13 pages.
(Continued)

*Primary Examiner* — Nimeshkumar D Patel
*Assistant Examiner* — Tarun Sinha
(74) *Attorney, Agent, or Firm* — Arch & Lake LLP

(57) ABSTRACT

A plug-in air quality detector, a control method, and a control circuit are provided in the field of air quality detection. The plug-in air quality detector comprises a casing, a sensor component, a control circuit and a connector component. The connector component includes a power supply terminal and a data terminal, and is configured to connect the plug-in air quality detector with a user device. As such, the detector may prompt a user of the air quality around the user without being configured with a dedicated power supply and a dedicated display screen, thereby achieving the effects of reducing the size and the weight of the air quality detector and improving the ease of use.

18 Claims, 8 Drawing Sheets

(51) Int. Cl.
*G01N 15/06* (2006.01)
*H04M 1/21* (2006.01)
*G01N 33/00* (2006.01)
*F24F 110/50* (2018.01)
*B60H 1/00* (2006.01)
*H04M 1/725* (2006.01)
*G01N 15/00* (2006.01)
*G01N 15/02* (2006.01)

(52) U.S. Cl.
CPC ..... *G01N 33/0027* (2013.01); *G01N 33/0062* (2013.01); *G01N 33/0073* (2013.01); *H04M 1/21* (2013.01); *B60H 1/008* (2013.01); *F24F 2110/50* (2018.01); *G01N 15/0205* (2013.01); *G01N 2001/2276* (2013.01); *G01N 2001/2285* (2013.01); *G01N 2015/0046* (2013.01); *G01N 2015/0693* (2013.01); *H04M 1/72527* (2013.01); *H04M 2250/12* (2013.01)

(58) Field of Classification Search
USPC .......................................................... 73/31.2
See application file for complete search history.

(56) References Cited

U.S. PATENT DOCUMENTS

| | | | |
|---|---|---|---|
| 2009/0109042 A1 | 4/2009 | Almiman | |
| 2014/0076022 A1* | 3/2014 | Ohlsson | G01N 33/4972 73/23.3 |
| 2015/0059437 A1* | 3/2015 | Son | G01N 33/0008 73/23.3 |
| 2015/0077737 A1 | 3/2015 | Belinsky et al. | |
| 2015/0212057 A1 | 7/2015 | Darveau | |

FOREIGN PATENT DOCUMENTS

| | | | |
|---|---|---|---|
| CN | 202854084 | * | 4/2013 |
| CN | 103645279 | A | 3/2014 |
| CN | 103868827 | A | 6/2014 |
| CN | 103884823 | A | 6/2014 |
| CN | 103954543 | A | 7/2014 |
| CN | 203772837 | U | 8/2014 |
| CN | 203869994 | U | 10/2014 |
| CN | 204008393 | U | 12/2014 |
| CN | 104502525 | A | 4/2015 |
| CN | 104677792 | A | 6/2015 |
| CN | 104836876 | A | 8/2015 |
| CN | 204649241 | U | 9/2015 |
| CN | 204789453 | U | 11/2015 |
| CN | 204902880 | U | 12/2015 |
| CN | 204922540 | U | 12/2015 |
| CN | 205038127 | U | 2/2016 |
| CN | 105891121 | A | 8/2016 |
| CN | 205538902 | U | 8/2016 |

OTHER PUBLICATIONS

First Office Action (including English translation) issued in corresponding Chinese Application No. 201610189032.X dated Jan. 29, 2018, 13 pages.

Extended European search report issued in corresponding European Application No. 17163267.2, dated Jul. 26, 2017, 8 pages.

* cited by examiner

PLUG-IN AIR QUALITY DETECTOR, CONTROL METHOD AND CONTROL DEVICE

CROSS-REFERENCE TO RELATED APPLICATION

This application is based on and claims the priority of the Chinese patent application No. CN201610189032.X, filed on Mar. 29, 2016, which is incorporated herein by reference in its entirety.

Technical Field

The present disclosure is related to the field of air quality detection, and more particularly to a plug-in air quality detector, a control method and a control device.

Background

With the rapid progress of urbanization and industrialization, urban air quality is facing a severe challenge. Thus, an air quality detector is required to detect air quality parameters in urban environments to determine whether it is needed to wear a mask, leave an area or take other measures.

In related arts, there are two types of air quality detectors, namely fixed air quality detectors and mobile air quality detectors. A fixed air quality detector can only detect an air quality parameter in a fixed area, while a mobile air quality detector can move freely to detect an air quality parameter in an environment of an area where it is located at any time. However, each existing mobile air quality detector needs a dedicatedly configured power supply and a dedicatedly configured display screen for displaying data, and is thus large and heavy and inconvenient for a user to carry every day.

SUMMARY

Embodiments of the present disclosure provide a plug-in air quality detector, a control method and a control device as follows.

According to a first aspect of the present disclosure, there is provided a plug-in air quality detector comprising a casing, a sensor component, a control circuit and a connector component. The sensor component and the control circuit are arranged inside the casing. The control circuit is electrically connected with the sensor component and the connector component respectively. The sensor component is configured to measure an air quality parameter of air around the plug-in air quality detector. The connector component is configured to connect the plug-in air quality detector with a user device, and comprises a power supply terminal and a data terminal.

According to a second aspect of the present disclosure, there is provided a plug-in air quality detector control method for use in a plug-in air quality detector according to the first aspect of the embodiments of the present disclosure. The method comprises: when the plug-in air quality detector is connected with the user device via the connector component, acquiring by the control circuit an air quality parameter of air around the plug-in air quality detector measured by the sensor component; and giving a prompt by the control circuit according to the air quality parameter, or sending by the control circuit the air quality parameter to the user device via the connector component.

According to a third aspect of the present disclosure, there is provided a control circuit for use in a plug-in air quality detector according to the first aspect of the embodiments of the present disclosure. The control circuit comprises an acquiring module and a prompting module or comprises the acquiring module and a sending module. The acquiring module is configured to acquire an air quality parameter of air around the plug-in air quality detector measured by the sensor component, when the plug-in air quality detector is connected with the user device via the connector component. The prompting module is configured to give a prompt according to the air quality parameter acquired by the acquiring module. The sending module is configured to send the air quality parameter acquired by the acquiring module to the user device via the connector component.

According to a fourth aspect of the present disclosure, there is provided a plug-in air quality detector control circuit for use in a plug-in air quality detector according to the first aspect of the embodiments of the present disclosure. The device comprises: a processor; and a memory configured to store instructions executable by the processor. The processor is configured to: when the plug-in air quality detector is connected with the user device via the connector component, acquire an air quality parameter of air around the plug-in air quality detector measured by a sensor component; and give a prompt according to the air quality parameter, or send the air quality parameter to the user device via the connector component.

It should be understood that both the foregoing general description and the following detailed description are only exemplary and explanatory and are not restrictive of the present disclosure.

BRIEF DESCRIPTION OF THE DRAWINGS

The accompanying drawings, which are incorporated in and constitute a part of this specification, illustrate embodiments consistent with the disclosure and, together with the description, serve to explain the principles of the disclosure.

DETAILED DESCRIPTION

When a user is travelling, the user may want to have an idea about the local air quality after getting to a new location. In this situation, the user may use a plug-in air quality detector with his user device to measure the local air quality. For example, the user may directly plug the plug-in air quality detector into a headset jack of the user device. After the user turns on the plug-in air quality detector, the control circuit in the plug-in air quality detector controls the sensor component to start working. After a preset time period, the plug-in air quality detector may give an alert to the user using an indicating lamp on the plug-in air quality detector. Alternatively or additionally, the plug-in air quality detector may activate an application in the user device and then instruct the user device to display the measured air quality in the application of the user device.

Reference will now be made in detail to exemplary embodiments, examples of which are illustrated in the accompanying drawings. The following description refers to the accompanying drawings in which the same numbers in different drawings represent the same or similar elements unless otherwise indicated. The implementations set forth in the following description of exemplary embodiments do not represent all implementations consistent with the disclosure. Instead, they are merely examples of apparatuses and methods consistent with aspects related to the disclosure as recited in the appended claims.

Figure 1:
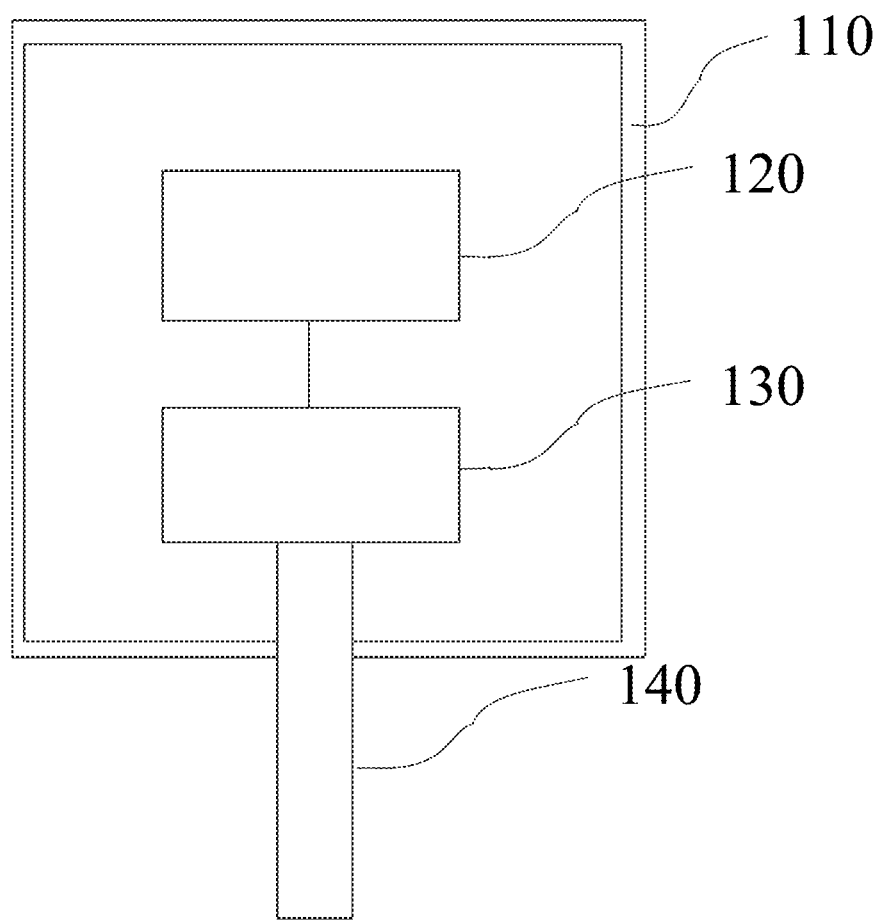
FIG. 1 is a structure diagram of a plug-in air quality detector according to one or more exemplary embodiments.

FIG. 1 is a structure diagram of a plug-in air quality detector according to an exemplary embodiment of the present disclosure. The plug-in air quality detector may comprise a casing 110, a sensor component 120, a control circuit 130, and a connector component 140.

The sensor component 120 and the control circuit 130 are arranged inside the casing 110.

The control circuit 130 is electrically connected with the sensor component 120 and the connector component 140 respectively.

The sensor component 120 is configured to measure an air quality parameter of air around the plug-in air quality detector. Here, the sensor component 120 may measure the air quality parameter of air in a region that is within a sphere with a radius less than about five meters. The air quality parameter may be more reliable for measuring the air quality within a sphere that has a radius less than about three meters. Here, the center of the sphere is the sensor component 120. The sensor component 120 may be used in an indoor setting.

The connector component 140 is configured to connect the plug-in air quality detector with a user device, and comprises a power supply terminal and a data terminal. For example, the connector component 140 may include one of the following: a universal serial bus (USB) connector, a micro USB connector, an earphone connector, a lightening connector, other any other connector that may be used to connect the user device with the plug-in air quality detector.

In one or more embodiments of the disclosure, the plug-in air quality detector includes the casing, the sensor component, the control circuit and the connector component. The connector component includes the power supply terminal and the data terminal and is configured to connect the plug-in air quality detector with the user device. As such, the detector may prompt a user of the air quality around him/her without being configured with a dedicated power supply and a dedicated display screen, thereby solving the problem in the prior art that an existing mobile air quality detector which needs to be provided with a dedicated power supply and a dedicated display screen for displaying data is so large and heavy that it is inconvenient for the user to carry the detector every day, and achieving the effects of reducing the size and the weight of the mobile air quality detector and improving the ease of use.

Figure 2:
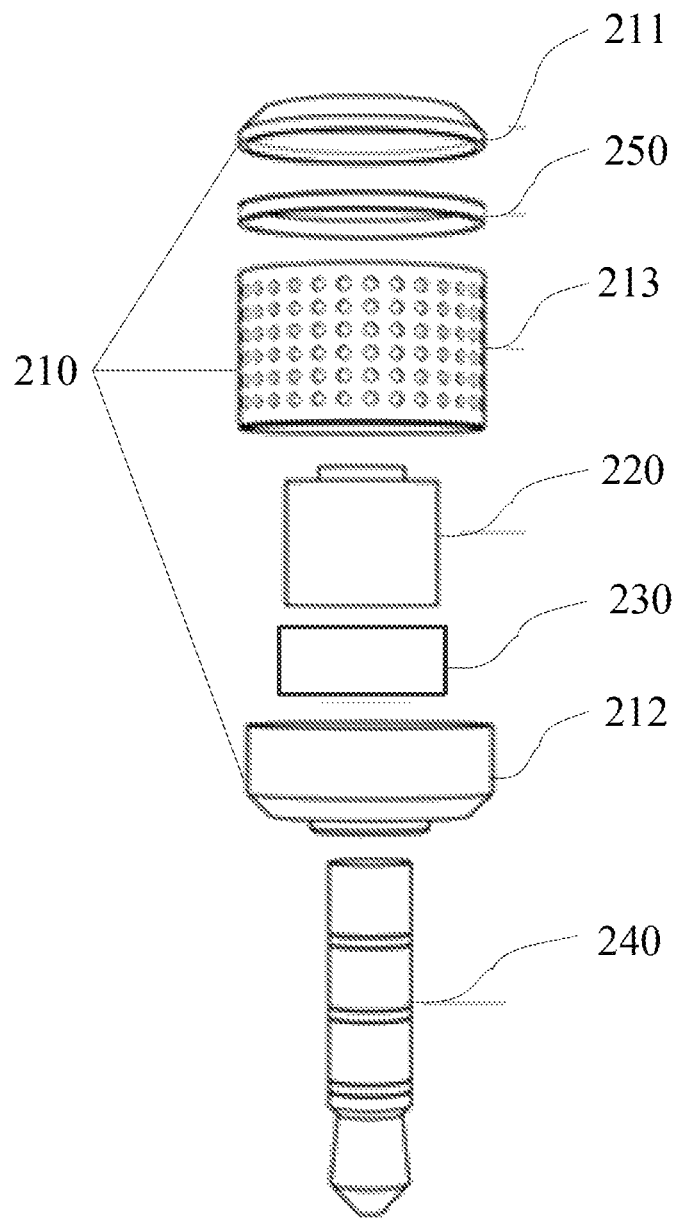
FIG. 2 is a structure diagram of a plug-in air quality detector according to one or more exemplary embodiments.

FIG. 2 is a structure diagram of a plug-in air quality detector according to another exemplary embodiment of the present disclosure. The plug-in air quality detector may comprise a casing 210, a sensor component 220, a control circuit 230, and a connector component 240.

The sensor component 220 and the control circuit 230 are arranged inside the casing 210.

One of functions of the casing 210 is to provide an accommodating space for the sensor component 220 and the control circuit 230. The casing 210 may be made of a lightweight material. The purpose of adopting the lightweight material to make the casing is to reduce the weight of the casing, so that the connector component is unlikely to suffer from a load caused by excessive weight after the plug-in air quality detector is plugged in a user device via the connector component, thereby prolonging the service life of the plug-in air quality detector.

Optionally, the lightweight material may be a synthetic resin or a metallic material.

The synthetic resin may be acrylonitrile-butadiene-styrene copolymer (ABS), acrylic or polypropylene. In addition, engineering plastics such as polycarbonate (PC), polyamide (PA), polyacetal polyoxy methylene (POM), polyphenylene oxide (PPO), PET, PBT, polyphenylene sulfide (PPS) and polyarylate may be also used as materials for making the casing 210.

The metallic material may be a light alloy, a light metal, a less dense metal or a less dense alloy. For example, the light alloy may be an aluminum alloy, a magnesium alloy or a titanium alloy, and the light metal may be aluminum or magnesium.

In addition to the above-described synthetic resins and metallic materials, the casing 210 may also be made of carbon fiber. The above materials are given as examples supposing the casing is made of a lightweight material, and there are other materials not limited by the present disclosure which can achieve the purpose of the present disclosure. To implement the present disclosure, one single type of material or multiple types of materials may be selected for use. The type(s) of material(s) selected for use is/are not restricted herein.

The control circuit 230 is electrically connected with the sensor component 220 and the connector component 240 respectively.

The control circuit 230 may include a chip with a control ability, a logic circuit group, an electronic component having a logic control ability, or a combination of the above hardware parts. After the control circuit 230 is electrically connected with the sensor component 220 and the connector component 240, the plug-in air quality detector can work under the control of the control circuit 230. The control circuit 230 can control the On/Off of the sensor component 220 and of an indicating lamp 250 in the plug-in air quality detector. Also, the control circuit 230 can send an air quality parameter acquired by the sensor component 220 to the user device. Alternatively, the control circuit 230 can determine whether the air quality parameter acquired by the sensor component 220 exceeds a preset value, output a warning message when the air quality parameter exceeds the preset value so that the light emitting mode of the indicating lamp 250 changes to a light emitting mode corresponding to the warning message, and output a normal message when the air quality parameter does not exceed the preset value so that the light emitting mode of the indicating lamp 250 changes to a light emitting mode corresponding to the normal message.

For the control circuit 230 to meet functions required by design of the present disclosure, in practical implementation, required functional circuits may be selected for use from combinational logic circuits and sequential logic circuits.

The control circuit may be composed of one or more of a resistor-transistor logic circuit, a diode-transistor logic circuit, an emitter function logic circuit, an emitter coupled logic circuit, a high-threshold logic circuit, an integrated injection logic circuit and a transistor-transistor logic circuit.

The sensor component 220 may measure an air quality parameter of air around the plug-in air quality detector. For example, the sensor component 220 may include at least one hardware component such as a light source configured to measure the air quality parameter using a light scattering method. That is, what the sensor component 220 senses is air around the plug-in air quality detector in which the sensor component 220 is arranged.

For instance, an example is given in which the sensor component 220 is used to measure a parameter about air pollution, where the parameter may include at least one of: a $CO_2$ level, a $CO_1$ level, pollen density, a PM2.5 value of air around the plug-in air quality detector, etc. In an implementable operation manner, a light scattering method can be used for measuring. The working principle of the sensor component 220 is as follows: an infrared light source (or a white light or laser source) is adopted; the infrared light intensity is measured in the direction perpendicular to a light path from the infrared light source; then the number of times the change of the infrared light intensity exceeds a preset threshold in a unit time is measured via a counter; and next a unified and standard concentration per unit mass is obtained by use of a conversion formula and a calibration method.

Besides the above light scattering method implementable by the sensor component 220, the sensor component 220 may also adopt a microscopy measuring method, a weighting measuring method, a differential mobility analyzer (DMA) measuring method (particle size analyzer measuring method), an inertial measuring method, a diffusion measuring method, a condensation nucleus counter (CNC) measuring method or the like to measure the PM2.5 value.

Here, by taking an example in which the sensor component 220 adopts the light scattering method for measuring, a working process of the sensor component 220 is introduced. When the sensor component 220 works, a particular laser beam is produced by a dedicated optical component integrated in the sensor component 220. Once a particulate matter passes through the laser, a change of intensity of the laser occurs in the direction perpendicular to a light path of the laser. When the change of the laser intensity is within a specified range corresponding to PM2.5 fine particulate matters, a counter will increment its counted value by one. After a certain time period specified for a timer passes, the PM2.5 value is calculated according to the value of the counter and the certain time period specified for the timer. Moreover, the counter and the timer may be integrated in the sensor component 220, or integrated in the control circuit 230. The present disclosure does not limit positions of components capable of functioning as the counter and the timer.

Optionally, the plug-in air quality detector provided by the present disclosure may be designed to detect only PM2.5 particulate matters, or may be designed to detect a variety of particulate matters with different diameter sizes. Thus, the sensor component 220 may be designed to have a single channel (for performing measurement for only particulate matters of the PM2.5 diameter) measuring structure, a two-channel measuring structure or a multi-channel measuring structure.

Meanwhile, the sensor component 220 provided by the present disclosure may also be designed to be provided with a component for detecting pollution gases, so as to perform measurement for the pollution gases in the air. These gases may comprise formaldehyde (HCHO), total volatile organic compounds (TVOC), ozone ($O_3$), nitrogen dioxide ($NO_2$) and the like.

The above-described measuring principles and structures of the sensor component are given as examples, and there are other measuring principles or structures not limited by the embodiments of the disclosure whereby the functions of the sensor component 220 provided by the present disclosure can be implemented.

The control circuit 230 is located inside the casing 210. For the purpose of saving space and reducing power consumption, the control circuit may be designed by use of an integrated circuit technology. In an implementation, the control circuit 230 may include at least one of the following: a Small Scale Integrated Circuit (SSIC), a Medium Scale Integrated circuit (MSIC), a Large Scale Integrated Circuit (LSIC), a Very Large Scale Integrated Circuit (VLSIC), a Ultra Large Scale Integrated Circuit (ULSIC), a Giga Scale Integrated Circuit (GSIC), or the like. The GSIC may also be referred to as a super large scale integrated circuit or an extremely ultra large scale integrated circuit.

The above descriptions of the circuit forms and design technologies of the control circuit 230 are given as examples, and there are other circuit forms and design technologies not limited by the present disclosure which can implement the functions of the control circuit 230 provided by the present disclosure.

The connector component 240 is configured to connect the plug-in air quality detector with a user device, and comprises a power supply terminal and a data terminal. The connector component 240 may be a phone connector, or a phone jack that may be inserted into a corresponding socket in a user device.

The connector component may include two functional interfaces, namely the power supply terminal and the data terminal. Through the power supply terminal, power required for operation of the plug-in air quality detector is supplied. Due to the existence of the power supply terminal, there is no need to arrange a power supply component for the plug-in air quality detector, and the space occupied by the plug-in air quality detector is significantly reduced. Through the data terminal, communication of data required to be communicated between the plug-in air quality detect and the user device can be performed. That is, the interface is used for not only sending data to the user device but also receiving data from the user device.

Alternatively or additionally, the plug-in air quality detector may further include the indicating lamp 250 having at least two light emitting modes. The indicating lamp 250 is electrically connected with the control circuit 230.

The function of the plug-in air quality detector is to alert a user as to whether an air quality parameter is greater than a preset parameter threshold. One of alerting manners is implemented by the indicating lamp 250 arranged in the plug-in air quality detector. The indicating lamp 250 has at least two light emitting modes. One of the light emitting modes represents that the detected air quality parameter is greater than the preset parameter threshold, and another of the light emitting modes represents that the air quality parameter is not greater than the preset parameter threshold.

Optionally, the casing 210 of the plug-in air quality detector includes an upper cover 211, a lower cover 212 and a lateral surrounding casing 213. The indicating lamp 250 may be arranged on the upper cover 211, or between the upper cover 211 and the lateral surrounding casing 213, or between the lower cover 212 and the lateral surrounding casing 213, or on the lateral surrounding casing 213. In summary, the indicating lamp 250 may be arranged in such a position that the indicating lamp can be seen by a user, and the position for arranging the indicating lamp 250 is not limited by the embodiment of the present disclosure.

Optionally, when in use, the upper cover 211, the lower cover 212 and the lateral surrounding casing 213 may be fixed in a non-detachable manner such as via an adhesive, welding or the like, or may be mounted in a user-detachable manner such as via magnetic force of magnets and metal plugs. The user-detachable manner enables the user to replace a damaged part in the plug-in air quality detector.

Referring to FIG. 2, the indicating lamp 250 is arranged between the upper cover 211 and the lateral surrounding casing 213. Alternatively, the indicating lamp 250 may be arranged between the lower cover 212 and the lateral surrounding casing 213.

Optionally, the sensor component 220 and the control circuit 230 of the plug-in air quality detector are fixed inside a space enclosed by the upper cover 211, the lower cover 212 and the lateral surrounding casing 213. A plurality of air holes are formed on the lateral surrounding casing 213.

Optionally, as the upper cover 211, the lower cover 212 and the lateral surrounding casing 213 are part of the casing 210, materials thereof may be the same as the above-described materials used for the casing 210.

Referring to FIG. 2, the plurality of air holes are formed on the lateral surrounding casing 213 for enabling the sensor component 220 located inside the casing 210 to be fully in contact with air around the plug-in air quality detector. Meanwhile, being located inside the space enclosed by the upper cover 211, the lower cover 212 and the lateral surrounding casing 213, the sensor component 220 is safe and unlikely to be damaged due to physical impact by external objects.

During design of the plurality of air holes on the lateral surrounding casing 213, the number of the air holes as well as the size of the air holes should be taken into consideration to enable the air holes to be distributed in the lateral surrounding casing 213 as evenly as possible, so that the air quality parameter of air around the plug-in air quality detector can be collected and detected relatively evenly.

Optionally, the connector component 240 of the plug-in air quality detector is located outside the space enclosed by the upper cover 211, the lower cover 212 and the lateral surrounding casing 213. An end of the connector component 240 which is connected with the control circuit 230 is fixed onto the lower cover 212.

In one or more embodiments, the control circuit 230 is located inside the casing 210. The control circuit 230 is connected with a user device through the connector component 240. Thus, the end of the connector component 240 connected with the control circuit 230 may be fixed onto the lower cover 212. One of the functions of the lower cover 212 is to protect a connection point connecting the end of the connector component 240 with the control circuit 230. Accordingly, a break is unlikely to occur at the connection point because of the lower cover 212.

Alternatively or additionally, the plug-in air quality detector further comprises a power button 260. The power button 260 is electrically connected with the control circuit 230.

Optionally, the power button 260 is arranged on the upper cover 211, or arranged on the lateral surrounding casing 213.

When the connector component of the plug-in air quality detector is plugged in the user device and the power supply terminal receives electric power, power is supplied to the plug-in air quality detector via the power supply terminal so long as a user presses the power button 260. Likewise, the plug-in air quality detector can be powered off by pressing the power button 260.

The power button 260 may be controlled in a pressing manner, a photoelectric sensing manner, a touching manner or the like, which is limited by the embodiment of the present disclosure.

Figure 3:
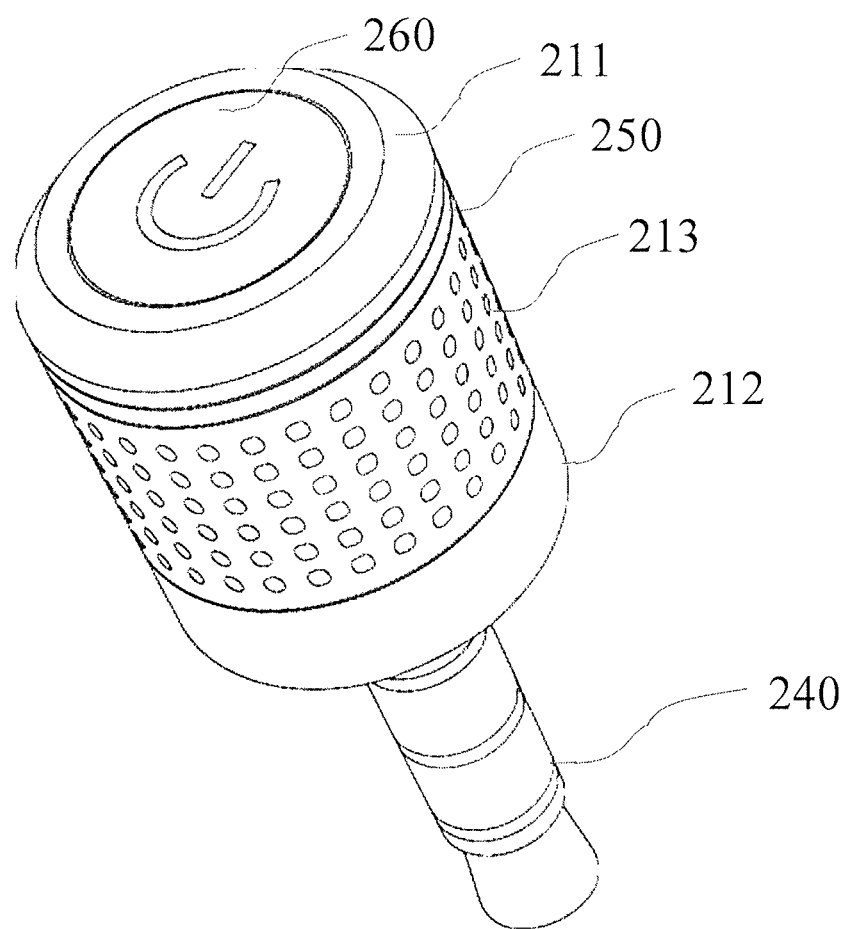
FIG. 3 is a schematic diagram illustrating an appearance of the plug-in air quality detector according to the exemplary embodiment corresponding to FIG. 2.

FIG. 3 is a schematic diagram illustrating an appearance of a plug-in air quality detector according to an embodiment of the present disclosure. In FIG. 3, the power button 260 is connected with the control circuit 230 (not shown in FIG. 3), and is arranged in a space enclosed by the upper cover 211. In the present embodiment, each of the upper cover 211 and the lower cover 212 may be designed as a hollow ring structure.

In addition, the indicating lamp 250 may also be arranged in an On/Off sign of the power button 260, and the On/Off sign may be made of a transparent material. When the indicating lamp 250 works, a light emitting mode of the indicating lamp 250 may be seen through the On/Off sign of the power button 260.

Optionally, the connector component of the plug-in air quality detector may be a plug component corresponding to a headset jack on the user device, or a plug component corresponding to a universal serial bus (USB) jack on the user device.

When the connector component of the plug-in air quality detector is the plug component corresponding to the headset jack on the user device, the plug component corresponding to the headset jack may be a 3.5-mm coaxial audio plug or a coaxial audio plug in accordance with another specification.

Also, the connector component may be the plug component corresponding to the universal serial bus (USB) jack on the user device. As USB jacks are different in standards, connector components for the USB jacks in practical use are also different. Optionally, the plug component corresponding to the USB jack may be a Mini-USB interface plug, a Micro-USB interface plug, a Type-C interface plug or the like.

Figure 4:
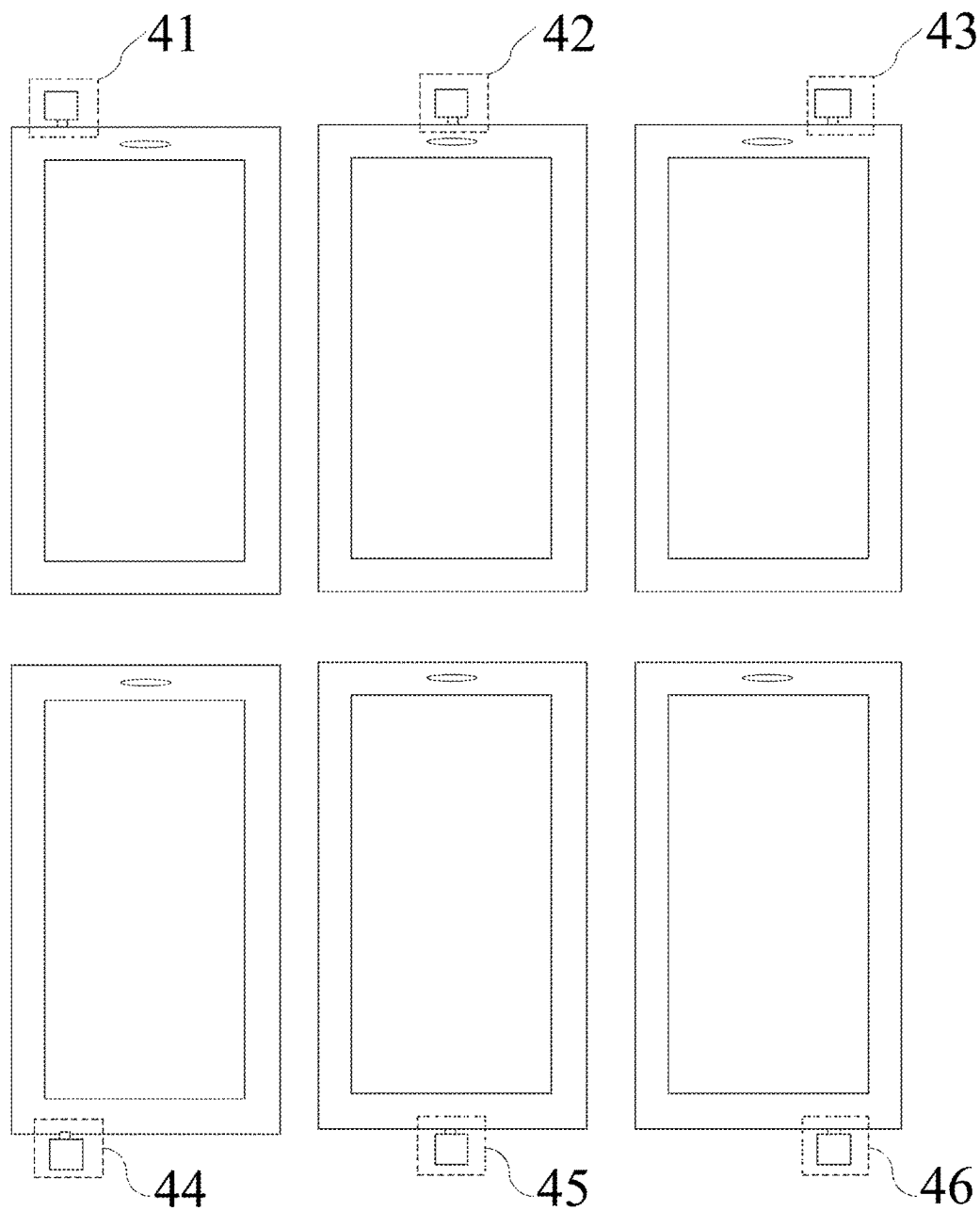
FIG. 4 is a schematic diagram illustrating plug-in positions of the plug-in air quality detector according to the exemplary embodiment corresponding to FIG. 2.

For connecting the plug-in air quality detector with a user device, a plug of the plug-in air quality detector may be directly inserted in a corresponding jack on the user device. FIG. 4 is a schematic diagram illustrating plug-in positions of the plug-in air quality detector according to an exemplary embodiment. Particularly, positional relationships between the plug-in air quality detector and the user device are shown in FIG. 4. As illustrated, the plug-in air quality detector may be arranged at any of positions 41, 42, 43, 44, 45 and 46. The specific position of the plug-in air quality detector depends on the position of the corresponding jack on the user device.

In the disclosure, the plug-in air quality detector includes the casing, the sensor component, the control circuit and the connector component. The connector component includes the power supply terminal and the data terminal and is configured to connect the plug-in air quality detector with a user device. When the plug-in air quality detector is connected with the user device via the connector component, the control circuit acquires the air quality parameter of the air around the plug-in air quality detector measured by the sensor component; and the control circuit gives a prompt according to the air quality parameter or sends the air quality parameter to the user device via the connector component. As such, the detector can prompt a user of the air quality around him/her without being configured with a dedicated power supply and a dedicated display screen, thereby solving the problem in the prior art that an existing mobile air quality detector which needs to be configured with a dedicated power supply and a dedicated display screen for displaying data is so large and heavy that it is inconvenient for the user to carry the detector every day, and achieving the effects of reducing the size and the weight of the air quality detector and improving the ease of use.

Figure 5:
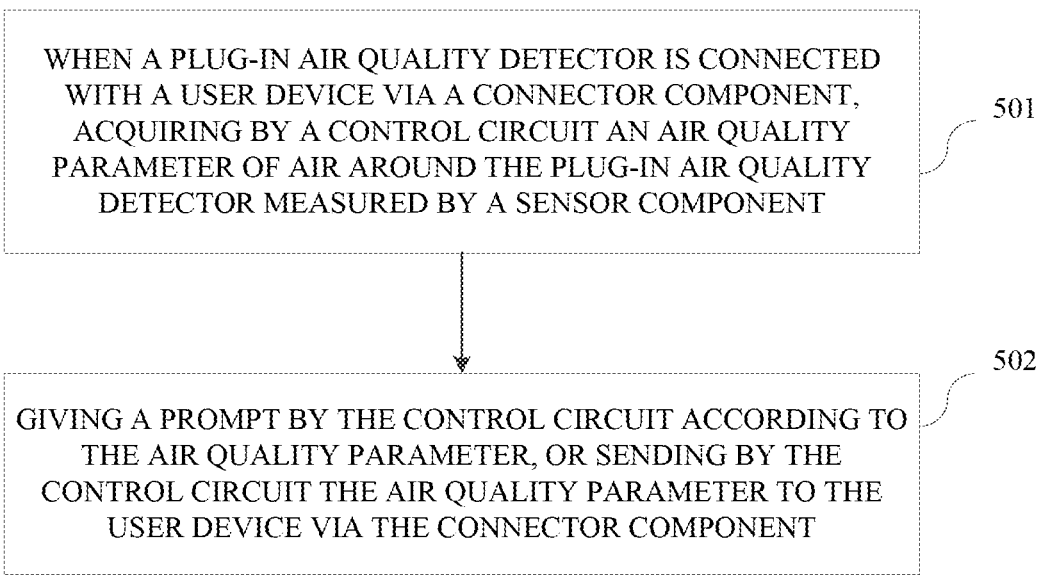
FIG. 5 is a flow chart of a plug-in air quality detector control method according to one or more exemplary embodiments.

FIG. 5 is a flow chart of a plug-in air quality detector control method according to one or more exemplary embodiments. The control method may be applied in the plug-in air quality detector shown in any of FIG. 1-3, and may include the following steps.

In step 501, when the plug-in air quality detector is connected with the user device via the connector component, the control circuit acquires an air quality parameter of air around the plug-in air quality detector measured by the sensor component.

In step 502, the control circuit gives a prompt according to the air quality parameter, or sends the air quality parameter to the user device via the connector component.

In the disclosure, a method is provided to control the plug-in air quality detector. When the plug-in air quality detector is connected with the user device via the connector component, the control circuit automatically acquires an air quality parameter of the air around the plug-in air quality detector acquired by the sensor component. The control circuit may give a prompt according to the air quality parameter. Alternatively or additionally, the control circuit may send the air quality parameter to the user device via the connector component. As such, the plug-in air quality detector can prompt a user of the air quality around him/her without being configured with a dedicated power supply and a dedicated display screen. The disclosed detector and method solve the problem in existing air quality detectors which need to be provided with a dedicated power supply and a dedicated display screen for displaying data. Further, the size and the weight of the disclosed air quality detector is reduced so that it is very convenient for the user to carry the disclosed air quality detector.

Figure 6:
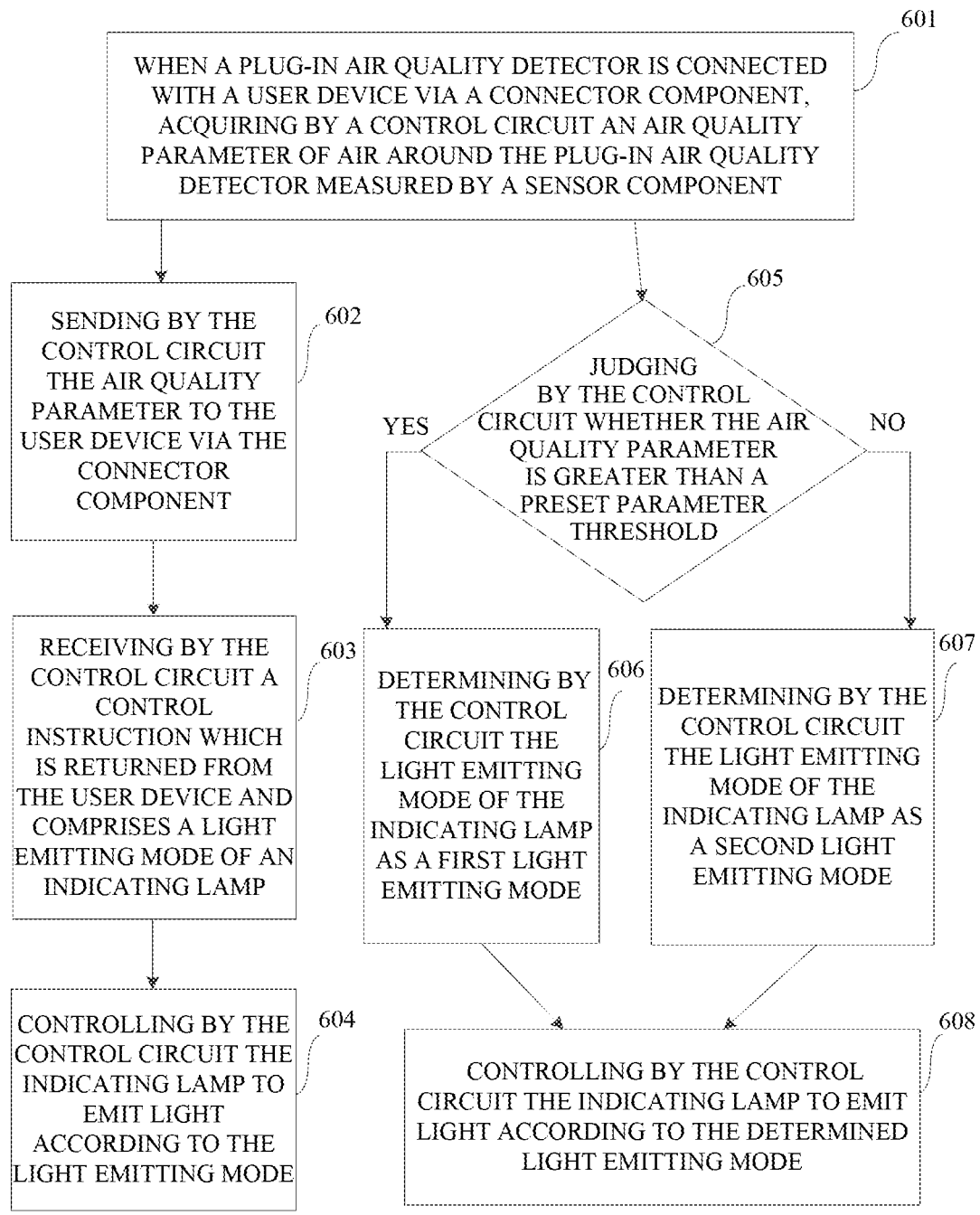
FIG. 6 is a flow chart of a plug-in air quality detector control method according to one or more exemplary embodiments.

For example, the connector component may include a pin-shaped plug corresponding to a headset jack (socket) on the user device. The method may further include: connecting the plug-in air quality detector with the user device by plugging the connector component into a headset jack on the user device; and sending by the control circuit the air quality parameter to the user device via the connector component connected with the headset jack on the user device FIG. 6 is a flow chart of a plug-in air quality detector control method according to one or more exemplary embodiments. The control method may be implemented in the plug-in air quality detector shown in any of FIG. 1-4, and may include at least the following steps.

In step 601, when the plug-in air quality detector is connected with a user device via the connector component, the control circuit acquires an air quality parameter of air around the plug-in air quality detector measured by the sensor component.

The air quality parameter of the air around the plug-in air quality detector, which is measured by the sensor component and acquired by the control circuit, may be a measured result value when a timer and a counter are integrated in the sensor component, or a signal which is transmitted into the control circuit by the sensor component in real time. In the latter case, calculation of the air quality parameter is performed cooperatively by the timer and the counter which are integrated in the control circuit.

In one or more embodiments, after the step 601 is performed, steps 602, 603, and 604 may be performed, and then step 605 and subsequent steps are performed.

In step 602, the control circuit sends the air quality parameter to the user device via the connector component.

After the step 602 is performed (correspondingly, after the user device receives the air quality parameter), the air quality parameter is compared with a preset parameter threshold to determine whether the air quality parameter is greater than the preset parameter threshold or not. When the air quality parameter is greater than the preset parameter threshold, a first instruction is generated correspondingly to instruct the plug-in air quality detector to emit light in a first light emitting mode. When the air quality parameter is not greater than the preset parameter threshold, a second instruction is generated correspondingly to instruct the plug-in air quality detector to emit light in a second light emitting mode. After that, the generated first instruction or second instruction is returned to the plug-in air quality detector.

In step 603, the control circuit receives a control instruction from the user device, where the control instruction includes one of light emitting modes of the indicating lamp.

The control instruction may include one of the at least two alternative light emitting modes, which are prominently distinguishable from each other. For example, in the first light emitting mode, a red light is emitted; and in the second light emitting mode, green light is emitted. Alternatively, in the first light emitting mode, light blinks; and in the second light emitting mode, light is emitted at a constant intensity.

In step 604, the control circuit controls the indicating lamp to emit light according to the light emitting mode.

In the plug-in air quality detector, the control circuit controls the indicating lamp to emit light according to the light emitting mode.

By performing the steps 601-604, the plug-in air quality detector control method according to the first possible implementation provided by one or more embodiments of the present disclosure is implemented.

In another possible implementation, the plug-in air quality detector control method is implemented by performing step 601 and steps 605 to 608 sequentially.

In step 605, the control circuit determines whether the air quality parameter is greater than the preset parameter threshold. If the determination is yes, step 606 is performed; if the determination is no, step 607 is performed.

The control circuit first makes a judgment for the air quality parameter calculated cooperatively by the counter and the timer. A time period set for the timer for detecting the air quality parameter may be 10 seconds, 15 seconds, 20 seconds, 30 seconds or the like, or any other time period suitable for the measurement purpose. The control circuit compares the air quality parameter with the preset parameter threshold to determine whether the air quality parameter is greater than the air quality parameter or not.

In step 606, the control circuit determines the light emitting mode of the indicating lamp as the first light emitting mode.

In step 607, the control circuit determines the light emitting mode of the indicating lamp as the second light emitting mode.

The first and second light emitting modes in the control instruction are prominently distinguishable from each other. For example, in the first light emitting mode, red light is emitted; and in the second light emitting mode, green light is emitted. Alternatively, in the first light emitting mode, light blinks; and in the second light emitting mode, light is emitted at a constant intensity. Alternatively, in the first light emitting mode, light emitting is cooperated with vibration of the user device or alerting by the device associated with the plug-in air quality detector; while in the second light emitting mode, there is no vibration of the user device or altering by the device associated with the plug-in air quality detector.

In step 608, the control circuit controls the indicating lamp to emit light according to the determined light emitting mode.

In a possible implementation scenario, the connector component of the plug-in air quality detector may be a headset plug and the user device may be a smart phone. After a user plugs the connector component of the plug-in air quality detector in a headset jack of the smart phone and presses the power button, the control circuit in the plug-in air quality detector controls the sensor component to start working and the timer starts timing at the same time. When a preset time period for the timer is 20 seconds, the indicating lamp of the plug-in air quality detector may give an alert the user correspondingly after 20 seconds. When an air quality parameter indicates that the air quality is relatively poor, e.g., a higher PM2.5 value, the indicating lamp may give a warning indication, such as emitting a blinking red light, and meanwhile the current air quality parameter may be displayed by a related application of the smart phone. Likewise, when an air quality parameter indicates that the air quality is good, e.g., a lower PM2.5 value, the indicating lamp may emit a normal light, such as green light, and meanwhile the current air quality parameter may be displayed by the related application of the smart phone.

After performing detection for the first time, the plug-in air quality detector can update the air quality parameter in real time, or update the air quality parameter at a preset time interval. For example, the air quality parameter may be updated every second in such a manner that old data detected within 19 previous seconds and new data detected within the present second are used to obtain an overall air quality parameter within a preset time interval of 20 seconds; or the air quality parameter may be updated every 5 seconds. The plug-in air quality detector is free of influence from a current interface of the phone, so that the user can use other applications. Once the quality parameter of air around the user exceeds a preset parameter value, the indicating lamp will give a prompt immediately, thereby enabling the user to make a timely response to a relatively poor air environment.

In the disclosure, according to the plug-in air quality detector control method, when the plug-in air quality detector is connected with the user device via the connector component, the control circuit may automatically acquire the air quality parameter of the air around the plug-in air quality detector measured by the sensor component if the plug-in air quality detector is turned on. The control circuit gives a prompt according to the air quality parameter or sends the air quality parameter to the user device via the connector component. As such, the plug-in air quality detector can prompt a user of the air quality around him/her without being configured with a dedicated power supply and a dedicated display screen. The disclosed detector and method solve the problem in the prior art that an existing air quality detector which needs to be provided with a dedicated power supply and a dedicated display screen for displaying data, where the existing air quality detector is so large and heavy that it is inconvenient for the user to carry the detector every day. The disclosed devices and methods achieve the effects of reducing the size and the weight of the air quality detector and improving the convenience for users.

Figure 7:
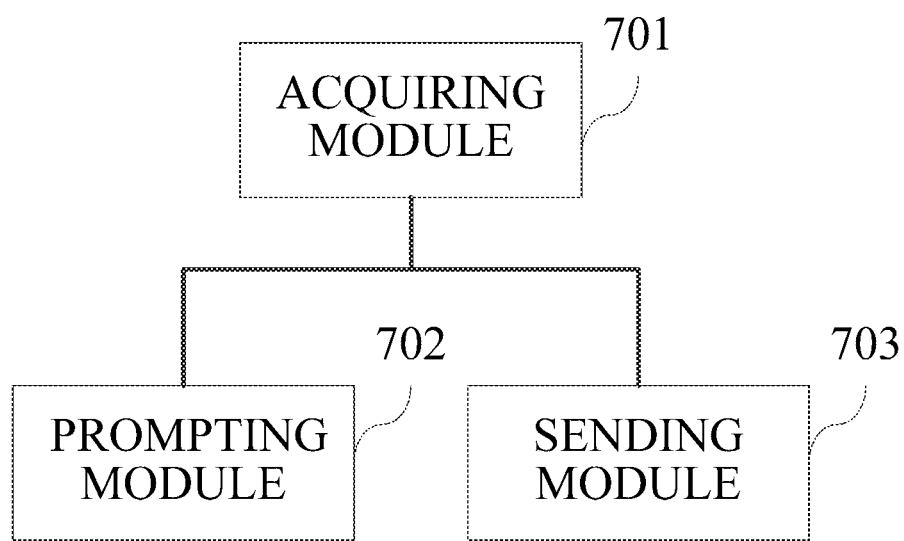
FIG. 7 is a block diagram of a control circuit according to one or more exemplary embodiments.

FIG. 7 is a block diagram of a control circuit according to one or more exemplary embodiments. The control circuit is applied in the plug-in air quality detector shown in any of FIG. 1-3. The control circuit includes an acquiring module 701 and a prompting module 702, or comprises the acquiring module 701 and a sending module 703.

The acquiring module 701 is configured to acquire an air quality parameter of air around the plug-in air quality detector measured by the sensor component when the plug-in air quality detector is connected with the user device via the connector component.

The prompting module 702 is configured to give a prompt according to the air quality parameter.

The sending module 703 is configured to send the air quality parameter to the user device via the connector component.

In the disclosure, the control circuit may be implemented with one or more circuitries, which include application specific integrated circuits (ASICs), digital signal processors (DSPs), digital signal processing devices (DSPDs), programmable logic devices (PLDs), field programmable gate arrays (FPGAs), controllers, micro-controllers, microprocessors, or other electronic components. The control circuit may use the circuitries in combination with the other hardware or software components for performing the above described methods. Each module, sub-module, unit, or sub-unit in the disclosure may be implemented at least partially using the one or more circuitries.

Figure 8:
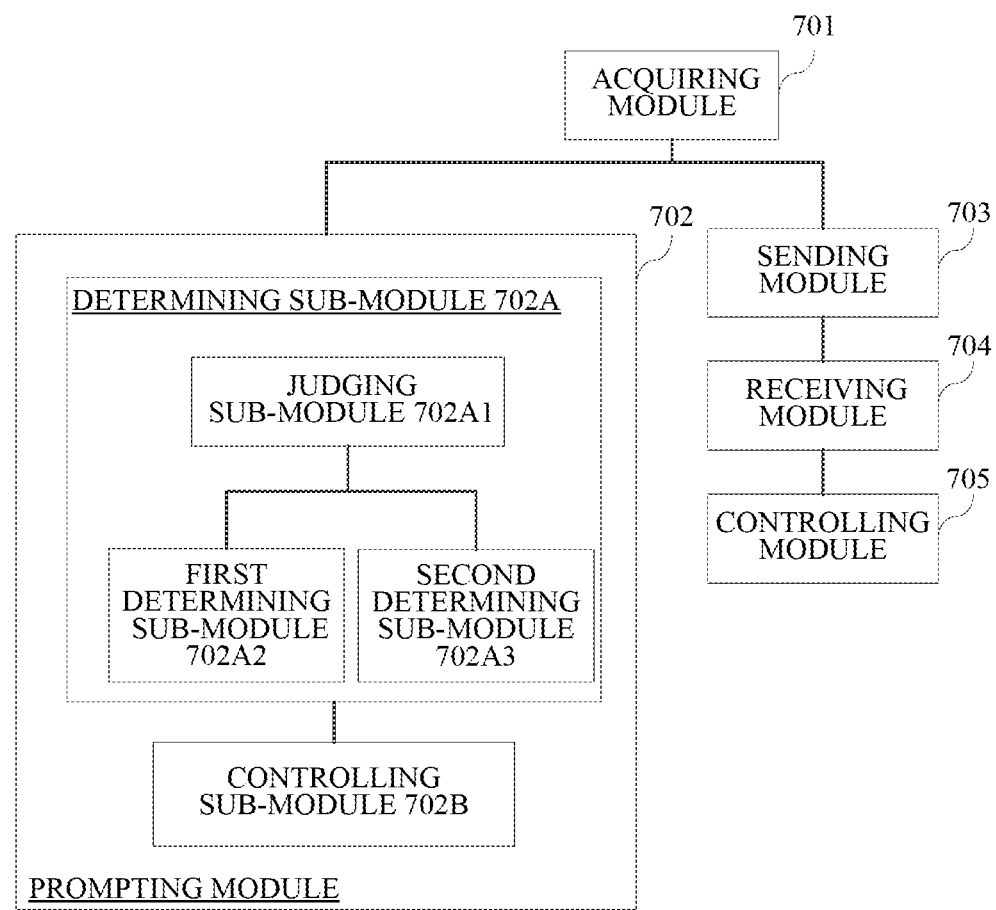
FIG. 8 is a block diagram of a control circuit according to one or more exemplary embodiments.

FIG. 8 is a block diagram of a control circuit according to one or more exemplary embodiments. The control circuit is applied in the plug-in air quality detector shown in any of FIG. 1-3. The control circuit comprises an acquiring module 701 and a prompting module 702, or comprises the acquiring module 701 and a sending module 703.

The acquiring module 701 is configured to acquire an air quality parameter of air around the plug-in air quality detector measured by a sensor component, when the plug-in air quality detector is connected with the user device via the connector component.

The prompting module 702 is configured to give a prompt according to the air quality parameter.

The sending module 703 is configured to send the air quality parameter to the user device via the connector component.

Optionally, the plug-in air quality detector comprises an indicating lamp. The prompting module 702 comprises: a determining sub-module 702*a* configured to determine a light emitting mode of the indicating lamp according to the air quality parameter acquired by the acquiring module; and a controlling sub-module 702*b* configured to control the indicating lamp to emit light according to the light emitting mode determined by the determining sub-module.

Optionally, when the indicating lamp at least has a first light emitting mode and a second light emitting mode, the determining sub-module 702*a* comprises a judging sub-module 702*a*1, a first determining sub-module 702*a*2 and a second determining sub-module 702*a*3.

The judging sub-module 702*a*1 is configured to determine whether the air quality parameter acquired by the acquiring module 701 is greater than a preset parameter threshold. The judging sub-module 702*a*1 may also determine whether the plug-in air quality detector includes an indicating lamp.

The first determining sub-module 702*a*2 is configured to determine the light emitting mode of the indicating lamp as the first light emitting mode, when the air quality parameter acquired by the acquiring module 701 is greater than the preset parameter threshold.

The second determining sub-module 702*a*3 is configured to determine the light emitting mode of the indicating lamp as the second light emitting mode, when the air quality parameter acquired by the acquiring module 701 is not greater than the preset parameter threshold.

Optionally, the plug-in air quality detector comprises an indicating lamp. The control circuit further comprises a receiving module 704 and a controlling module 705.

The receiving module 704 is configured to receive a control instruction which is returned from the user device and comprises a light emitting mode of the indicating lamp.

The controlling module 705 is configured to control the indicating lamp to emit light according to the light emitting mode received by the receiving module 704 after determining that the plug-in air quality detector includes the indicating lamp.

In the disclosure, when the plug-in air quality detector is connected with the user device via the connector component, the control circuit acquires an air quality parameter of the air around the plug-in air quality detector measured by the sensor component; and the control circuit gives a prompt according to the air quality parameter or sends the air quality parameter to the user device via the connector component. As such, the plug-in air quality detector can prompt a user of the air quality around him/her without being provided with a dedicated power supply and a dedicated display screen, thereby solving the problem in the prior art that an existing mobile air quality detector which needs to be provided with a dedicated power supply and a dedicated display screen for displaying data is so large and heavy that it is inconvenient for the user to carry the detector every day, and achieving the effects of reducing the size and the weight of the air quality detector and improving the ease of use.

It should be noted that, when the apparatuses provided by the above embodiments implement their functions, the above division into various functional modules is just described by way of example. In practical application, the above functions may be performed by different functional modules, that is, the internal structure of these apparatuses may be divided into different functional modules to realize all or part of the above-described functions.

With respect to the apparatuses in the above embodiments, the specific manners for individual modules therein to perform operations have been described in detail in the embodiments of the related methods, and will not be elaborated herein.

An exemplary embodiment of the present disclosure further provides a control device for the plug-in air quality detector shown in any of FIG. 1-3. The device is capable of implementing the plug-in air quality detector control methods provided by the embodiments of the present disclosure, and comprises a processor and a memory configured to store instructions executable by the processor. The processor is configured to: acquire an air quality parameter of air around the plug-in air quality detector measured by the sensor component when the plug-in air quality detector is connected with the user device via the connector component; and give a prompt according to the air quality parameter, or send the air quality parameter to the user device via the connector component.

Alternatively or additionally, the plug-in air quality detector may include an indicating lamp. Giving a prompt according to the air quality parameter comprises: determining a light emitting mode of the indicating lamp according to the air quality parameter; and controlling the indicating lamp to emit light according to the determined light emitting mode.

Alternatively or additionally, the indicating lamp at least has a first light emitting mode and a second light emitting mode. Determining the light emitting mode of the indicating lamp according to the air quality parameter comprises: determining whether the air quality parameter is greater than a preset parameter threshold; determining the light emitting mode of the indicating lamp as the first light emitting mode when the air quality parameter is greater than the preset parameter threshold, or determining the light emitting mode of the indicating lamp as the second light emitting mode when the air quality parameter is not greater than the preset parameter threshold.

Alternatively or additionally, the plug-in air quality detector may include an indicating lamp. After sending the air quality parameter to the user device via the connector component, the processor is further configured to: determine whether the plug-in air quality detector includes an indicating lamp, receive a control instruction returned from the user device and comprises a light emitting mode of the indicating lamp; and control the indicating lamp to emit light according to the light emitting mode after determining that the plug-in air quality detector comprises the indicating lamp.

The terminology used in the present disclosure is for the purpose of describing exemplary embodiments only and is not intended to limit the present disclosure. As used in the present disclosure and the appended claims, the singular forms "a," "an" and "the" are intended to include the plural forms as well, unless the context clearly indicates otherwise. It shall also be understood that the terms "or" and "and/or" used herein are intended to signify and include any or all possible combinations of one or more of the associated listed items, unless the context clearly indicates otherwise.

It shall be understood that, although the terms "first," "second," "third," etc. may be used herein to describe various information, the information should not be limited by these terms. These terms are only used to distinguish one category of information from another. For example, without departing from the scope of the present disclosure, first information may be termed as second information; and similarly, second information may also be termed as first information. As used herein, the term "if" may be understood to mean "when" or "upon" or "in response to" depending on the context.

Reference throughout this specification to "one embodiment," "an embodiment," "exemplary embodiment," or the like in the singular or plural means that one or more particular features, structures, or characteristics described in connection with an embodiment is included in at least one embodiment of the present disclosure. Thus, the appearances of the phrases "in one embodiment" or "in an embodiment," "in an exemplary embodiment," or the like in the singular or plural in various places throughout this specification are not necessarily all referring to the same embodiment. Furthermore, the particular features, structures, or characteristics in one or more embodiments may be combined in any suitable manner.

Other embodiments of the disclosure will be apparent to those skilled in the art from consideration of the specification and practice of the disclosure disclosed here. This application is intended to cover any variations, uses, or adaptations of the disclosure following the general principles thereof and including such departures from the present disclosure as come within known or customary practice in the art. It is intended that the specification and examples be considered as exemplary only, with a true scope and spirit of the disclosure being indicated by the following claims.

It will be appreciated that the present disclosure is not limited to the exact embodiments described above and illustrated in the accompanying drawings, and that various modifications and changes can be made without departing from the scope thereof. It is intended that the scope of the disclosure is only limited by the appended claims.

The invention claimed is:

1. A plug-in air quality detector, comprising:
   a sensor component and a control circuit disposed inside a casing; and
   a connector component comprising a power supply terminal and a data terminal, the connector component being configured to connect the plug-in air quality detector with a user device, and being a plug component corresponding to a headset jack on the user device or corresponding to a universal serial bus jack on the user device,
   wherein power required for operation of the plug-in air quality detector is supplied through the power supply terminal;
   wherein the control circuit is electrically connected with the sensor component and the connector component respectively, wherein the sensor component comprises a multi-channel measuring structure for detecting particulate matters with different diameter sizes; and
   wherein the sensor component is configured to periodically measure an air quality parameter of air around the plug-in air quality detector at a preset time interval.

2. The plug-in air quality detector of claim 1, further comprising an indicating lamp having at least two light emitting modes, wherein the indicating lamp is electrically connected with the control circuit.

3. The plug-in air quality detector of claim 2, wherein the casing comprises an upper cover, a lower cover, and a lateral surrounding casing, and
   wherein the indicating lamp is arranged at least partially in the upper cover.

4. The plug-in air quality detector of claim 3, wherein the sensor component and the control circuit are fixed inside a space enclosed by the upper cover, the lower cover, and the lateral surrounding casing, and the lateral surrounding casing comprises a plurality of holes therein.

5. The plug-in air quality detector of claim 3, wherein the connector component is located outside a space enclosed by the upper cover, the lower cover, and the lateral surrounding casing, and an end of the connector component that is connected with the control circuit is fixed onto the lower cover.

6. The plug-in air quality detector of claim 3, further comprising a power button, wherein the power button is electrically connected with the control circuit.

7. The plug-in air quality detector of claim 6, wherein the power button is arranged on the upper cover or the lateral surrounding casing.

8. The plug-in air quality detector of claim 1, further comprising an indicating lamp having at least two light emitting modes,
   wherein the casing comprises an upper cover, a lower cover, and a lateral surrounding casing, and
   wherein the indicating lamp is arranged between the upper cover and the lateral surrounding casing.

9. The plug-in air quality detector of claim 1, further comprising an indicating lamp having at least two light emitting modes,
   wherein the casing comprises an upper cover, a lower cover, and a lateral surrounding casing, and
   wherein the indicating lamp is arranged between the lower cover and the lateral surrounding casing.

10. A method, comprising:
    connecting, a plug-in air quality detector comprising: a connector component, a sensor component, and a control circuit disposed inside a casing, with a user device via the connector component, wherein the control circuit is electrically connected with the sensor component and the connector component respectively, and the connector component comprises a power supply terminal and a data terminal, the connector component is configured to connect the plug-in air quality detector with the user device, and the connector component is a plug component corresponding to a headset jack on the user device or corresponding to a universal serial bus jack on the user device; wherein power required for operation of the plug-in air quality detector is supplied through the power supply terminal, wherein the sensor component comprises a multi-channel measuring structure for detecting particulate matters with different diameter sizes;
    acquiring, by the control circuit, an air quality parameter of air around the plug-in air quality detector measured periodically by the sensor component at a preset time interval; and
    giving a prompt by the control circuit according to the air quality parameter.

11. The method of claim 10, wherein the plug-in air quality detector comprises an indicating lamp, and giving the prompt by the control circuit according to the air quality parameter comprises:
    determining a light emitting mode of the indicating lamp according to the air quality parameter; and
    controlling the indicating lamp to emit light according to the determined light emitting mode.

12. The method of claim 11, wherein the indicating lamp at least has a first light emitting mode and a second light emitting mode, and determining the light emitting mode of the indicating lamp according to the air quality parameter comprises:
    determining whether the air quality parameter is greater than a preset parameter threshold;
    when the air quality parameter is greater than the preset parameter threshold, determining the light emitting mode of the indicating lamp as the first light emitting mode; and
    when the air quality parameter is not greater than the preset parameter threshold, determining the light emitting mode of the indicating lamp as the second light emitting mode.

13. The method of claim 10, wherein the plug-in air quality detector comprises an indicating lamp, and wherein the method further comprises:
    Sending, by the control circuit, the air quality parameter to the user device via the connector component;
    receiving a control instruction from the user device, the control instruction comprising a light emitting mode of the indicating lamp; and
    controlling the indicating lamp to emit light according to the light emitting mode.

14. The method of claim 10, further comprising:
    connecting the plug-in air quality detector with the user device by plugging the connector component into the headset jack on the user device; and
    sending, by the control circuit, the air quality parameter to the user device via the connector component connected with the headset jack on the user device.

15. A control circuit, the control circuit comprising:
    a processor that is electrically connected with a sensor component and a connector component in a plug-in air quality detector, wherein the connector component comprises a power supply terminal and a data terminal, the connector component is configured to connect the plug-in air quality detector with a user device, and the connector component is a plug component corresponding to a headset jack on the user device or corresponding to a universal serial bus jack on the user device; wherein power required for operation of the plug-in air quality detector is supplied through the power supply terminal, wherein the sensor component comprises a multi-channel measuring structure for detecting particulate matters with different diameter sizes; and a memory configured to store instructions executable by the processor, wherein the processor is configured to:

when the plug-in air quality detector is connected with the user device via the connector component in the plug-in air quality detector, acquire an air quality parameter of air around the plug-in air quality detector periodically measured at a preset time interval by the sensor component; and give a prompt according to the air quality parameter.

16. The control circuit according to claim 15, wherein the processor is further configured to:

determine whether the plug-in air quality detector comprises an indicating lamp;

determine a light emitting mode of the indicating lamp according to the air quality parameter; and control the indicating lamp to emit light according to the determined light emitting mode after determining that the plug-in air quality detector comprises the indicating lamp.

17. The control circuit according to claim 16, wherein the processor is further configured to:

determine whether the air quality parameter is greater than a preset parameter threshold;

when the air quality parameter is greater than the preset parameter threshold, determine the light emitting mode of the indicating lamp as a first light emitting mode; and when the air quality parameter is not greater than the preset parameter threshold, determine the light emitting mode of the indicating lamp as a second light emitting mode.

18. The control circuit according to claim 15, wherein the processor is further configured to:

send the air quality parameter to the user device via the connector component;

determine whether the plug-in air quality detector comprises an indicating lamp;

receive a control instruction from the user device, the control instruction comprising a light emitting mode of the indicating lamp; and control the indicating lamp to emit light according to the light emitting mode after determining that the plug-in air quality detector comprises the indicating lamp.

* * * * *